(12) United States Patent
Lee et al.

(10) Patent No.: US 11,142,695 B2
(45) Date of Patent: Oct. 12, 2021

(54) ANTI-OXIDANT COMPOUNDS AND COMPOSITIONS

(71) Applicants: Duk Hi Lee, Anaheim, CA (US); Arthur Lee, San Carlos, CA (US)

(72) Inventors: Duk Hi Lee, Anaheim, CA (US); Arthur Lee, San Carlos, CA (US)

( * ) Notice: Subject to any disclaimer, the term of this patent is extended or adjusted under 35 U.S.C. 154(b) by 0 days.

(21) Appl. No.: 16/716,788

(22) Filed: Dec. 17, 2019

(65) Prior Publication Data
US 2021/0179938 A1    Jun. 17, 2021

(51) Int. Cl.
| | | |
|---|---|---|
| *C09K 15/30* | (2006.01) | |
| *C07D 251/32* | (2006.01) | |
| *C07D 251/66* | (2006.01) | |
| *C07D 251/54* | (2006.01) | |
| *C07D 251/24* | (2006.01) | |
| *C07F 9/12* | (2006.01) | |
| *C07F 9/40* | (2006.01) | |
| *C10M 133/42* | (2006.01) | |
| *C10M 137/04* | (2006.01) | |
| *C10M 137/12* | (2006.01) | |
| *C07D 251/18* | (2006.01) | |
| *C10N 30/10* | (2006.01) | |

(52) U.S. Cl.
CPC ............ *C09K 15/30* (2013.01); *C07D 251/18* (2013.01); *C07D 251/24* (2013.01); *C07D 251/32* (2013.01); *C07D 251/54* (2013.01); *C07D 251/66* (2013.01); *C07F 9/12* (2013.01); *C07F 9/40* (2013.01); *C10M 133/42* (2013.01); *C10M 137/04* (2013.01); *C10M 137/12* (2013.01); *C10M 2215/222* (2013.01); *C10M 2223/04* (2013.01); *C10M 2223/06* (2013.01); *C10N 2030/10* (2013.01)

(58) Field of Classification Search
CPC .. C07D 251/18; C07D 251/24; C07D 251/32; C07D 251/54; C07D 251/66; C07F 9/12; C07F 9/40; C09K 15/30; C10M 133/42; C10M 137/04; C10M 137/12; C10M 2215/222; C10M 2223/04; C10M 2223/06; C10N 2030/10
See application file for complete search history.

(56) References Cited

U.S. PATENT DOCUMENTS

| | | | | |
|---|---|---|---|---|
| 3,819,574 | A | * 6/1974 | Brown | ........... C08K 5/46 524/83 |
| 7,597,967 | B2 | * 10/2009 | Kondakova | ........... C09K 11/06 313/504 |
| 2010/0317754 | A1 | * 12/2010 | Nien | ........... E06B 9/266 521/79 |

(Continued)

FOREIGN PATENT DOCUMENTS

EP        0002269 A1 *  6/1979  ............. C09K 15/30

OTHER PUBLICATIONS

Chimenti, F., Bolasco, A., Secci, D. Chimenti, P., Granese, A., Carradori, S., Yanez, M., Orallo, F., Ortuso, F., Alcaro, S., "Investigations on the 2-thiazolylhydrazyne scaffold: Synthesis and molecular modeling of selective human monoamine oxidase inhibitors", Bioorg. Med. Chem., 18, 2010, 5715-5723 (Year: 2010).*

(Continued)

*Primary Examiner* — James C Goloboy
(74) *Attorney, Agent, or Firm* — Dennis P. Clarke

(57) ABSTRACT

Trisubstituted triazine antioxidants.

7 Claims, 14 Drawing Sheets

(56) References Cited

U.S. PATENT DOCUMENTS

2017/0211860 A1* 7/2017 Appler ............... C10M 171/008

OTHER PUBLICATIONS

Arkema product brochure "Hydrazine and Derivatives" retrieved from the Internet at <https://www.arkema.com.cn/export/shared/content/media/downloads/products-documentations/thiochemicals/brochure-Hydrazine.pdf> on Feb. 13, 2021 (Year: 2021).*
Sigma-Aldrich product page for Hydrazine monohydrate, retrieved from the Internet at <https://www.sigmaaldrich.com/catalog/product/sial/207942?lang=en&region=US> on Feb. 13, 2021. (Year: 2021).*

* cited by examiner

ANTI-OXIDANT COMPOUNDS AND COMPOSITIONS

BACKGROUND OF THE INVENTION

The invention relates to novel substituted triazines and their utility as anti-oxidants.

BRIEF SUMMARY OF THE INVENTION

One embodiment of the invention relates to compounds having the formula:

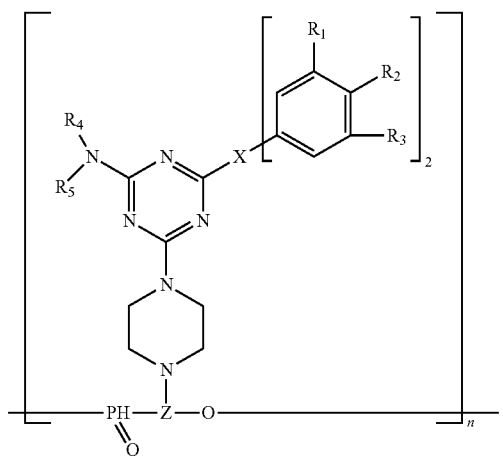

wherein:
X and Z are each CH,
$R_4$ and $R_5$ are aryl groups, such as, for example, phenyl groups,
$R_1$ and $R_3$ are bulky, sterically hindering alkyl groups such as, for example, t-butyl groups,
$R_2$ is OH, and
n=1-10.

Additional embodiments of the invention relate to compositions of matter containing the triazines of the invention adapted for admixture with a material subject to deterioration by oxidation, as well as compositions of matter comprising a material subject to oxidation and an antioxidant amount of the above described composition containing a substituted triazine of the invention or the substituted triazine itself and articles of manufacture comprising packaging material containing the above described composition containing a substituted triazine of the invention or the substituted triazine itself, wherein the packaging material contains instructions for the use thereof as an anti-oxidant

DETAILED DESCRIPTION OF THE INVENTION

Figure 1A:
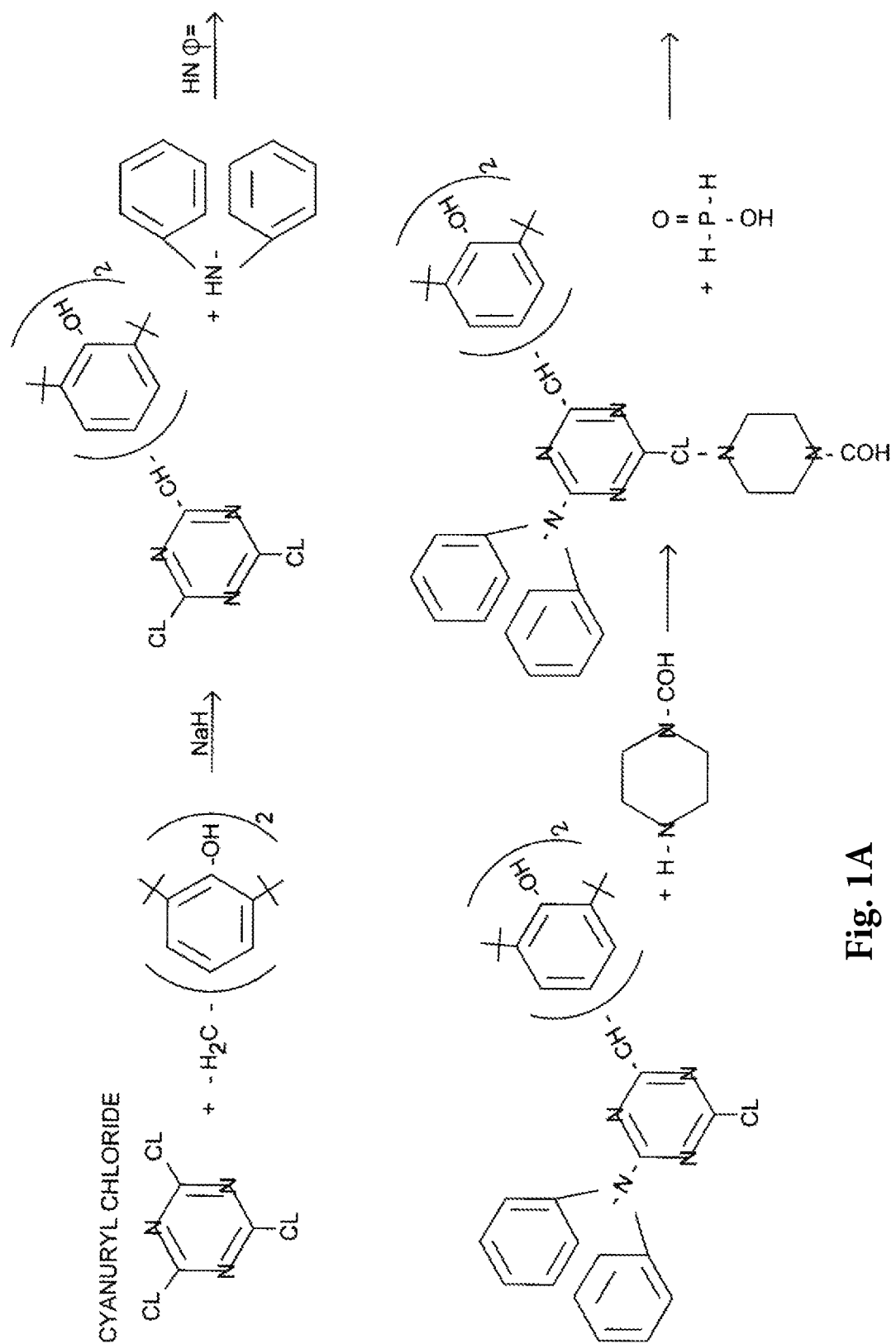
FIGS. 1A-13 depict exemplary reaction schemes for the preparation of the compounds of the invention.
Figure 1B:
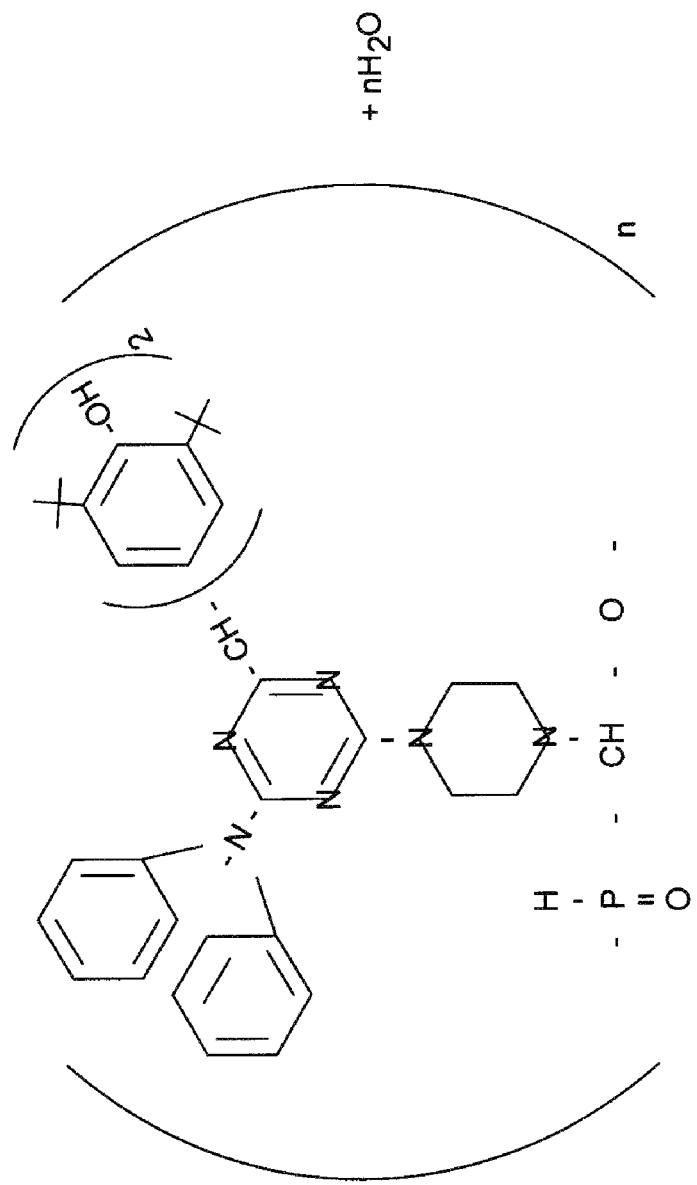
Figure 2:
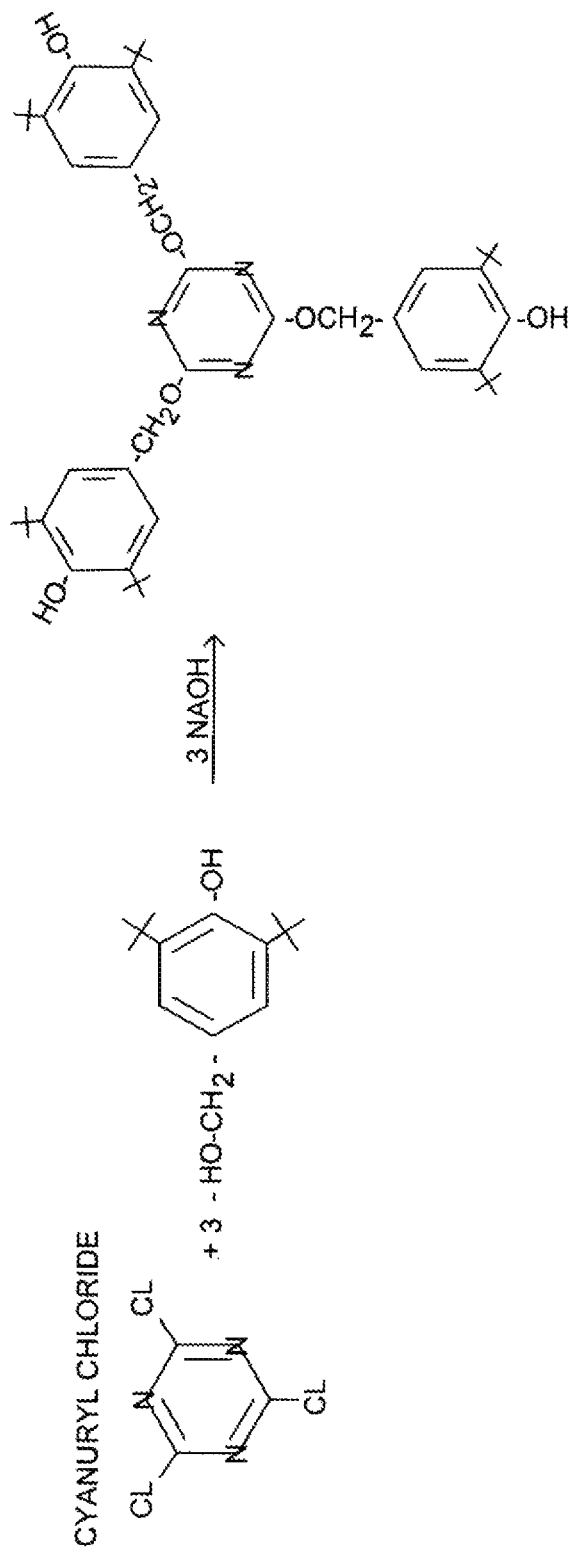
Figure 3:
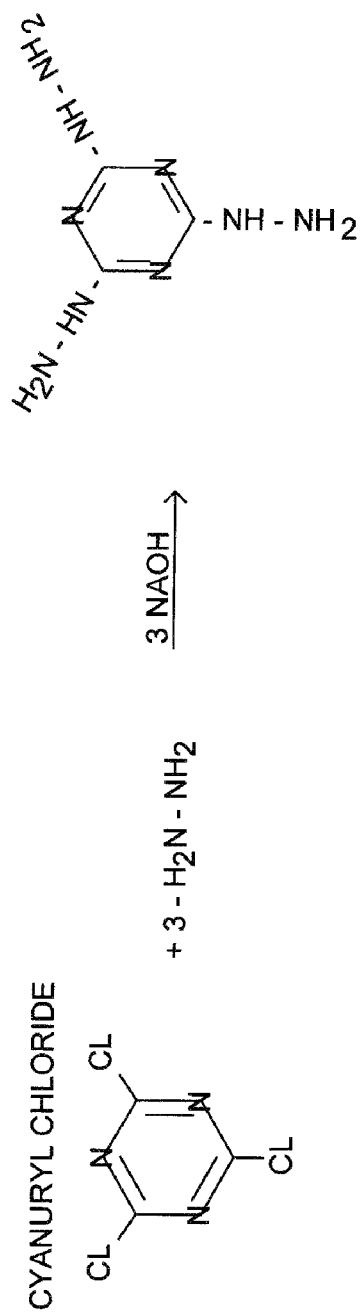
Figure 4:
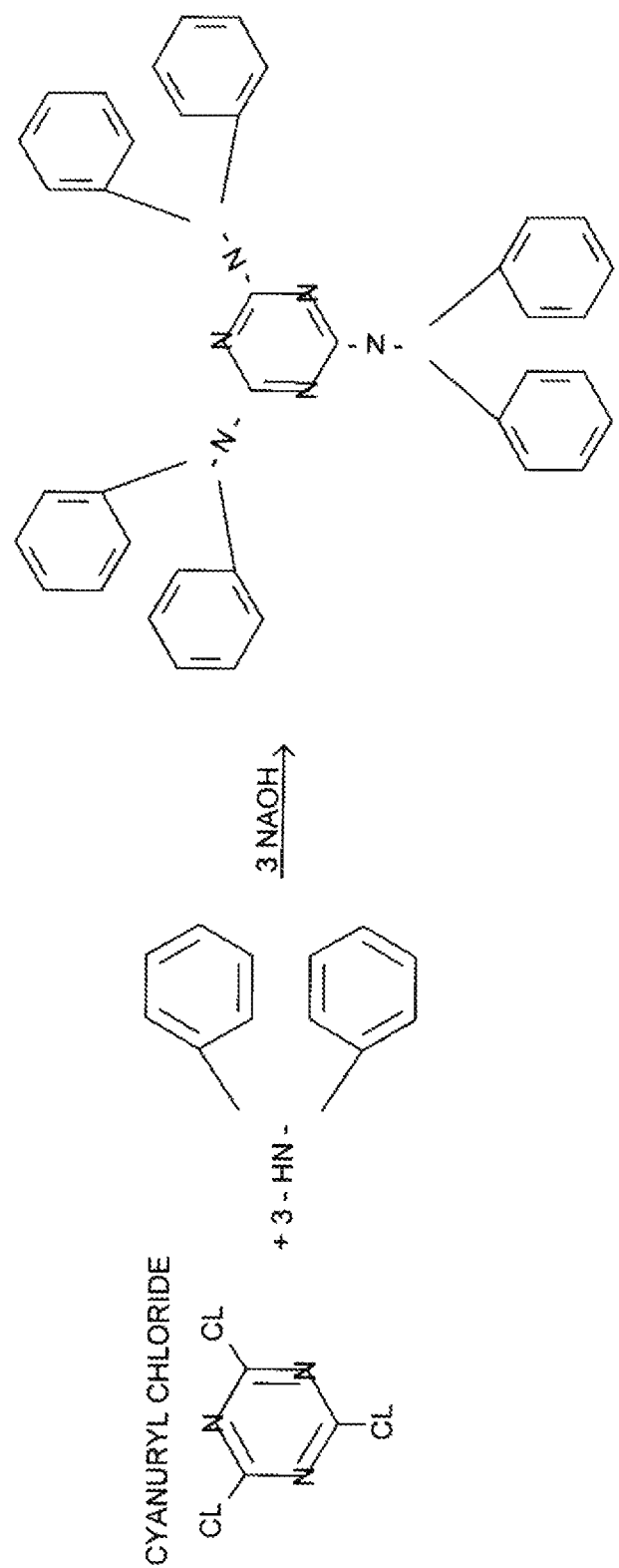
Figure 5:
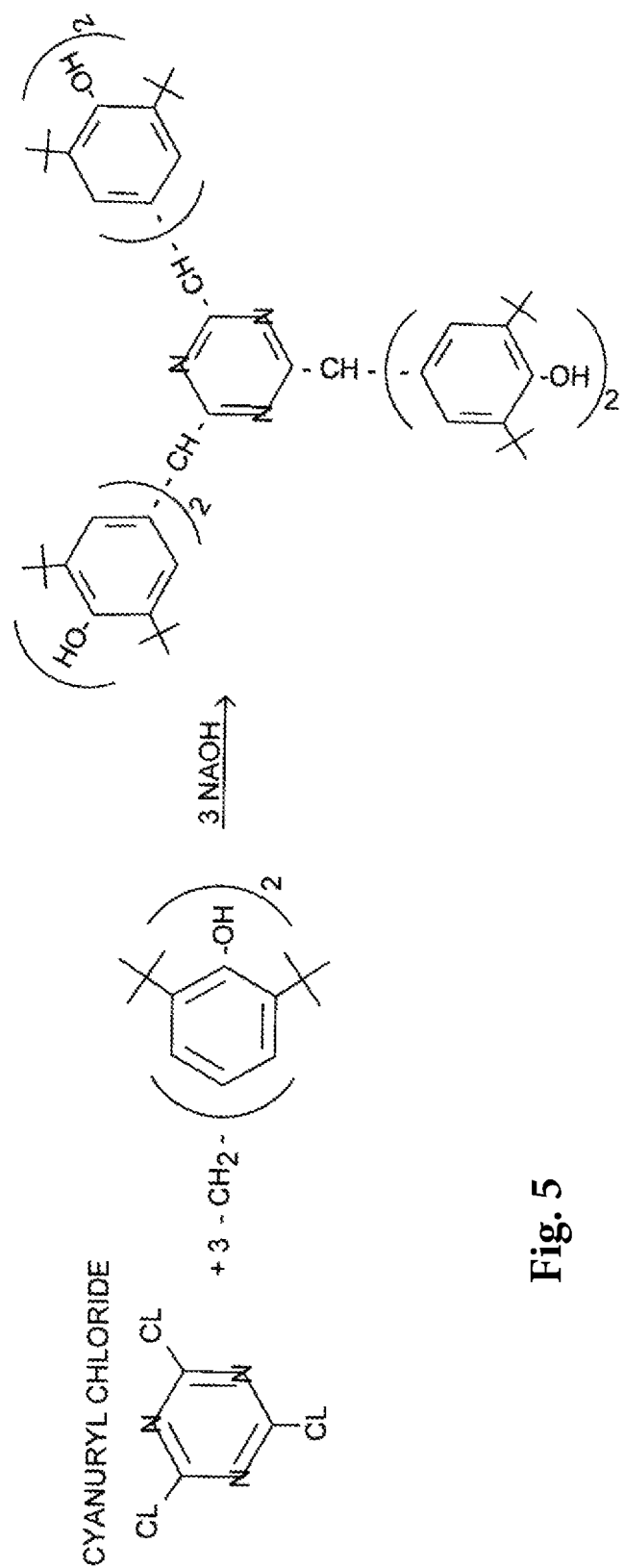
Figure 6:
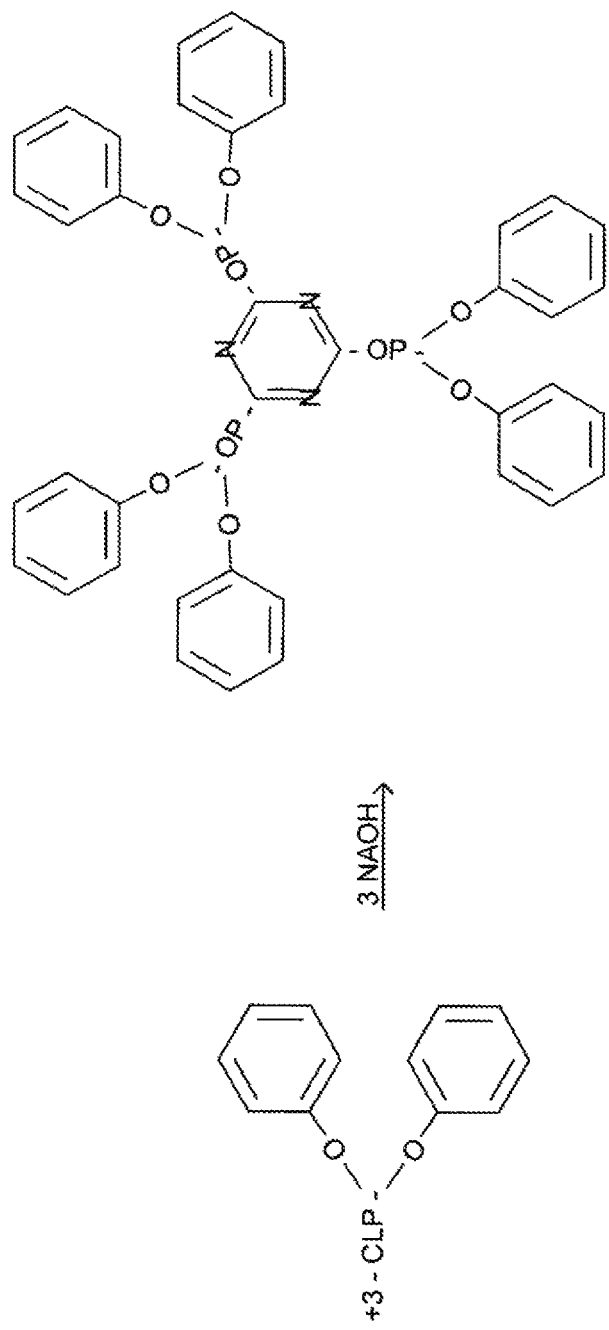
Figure 6:
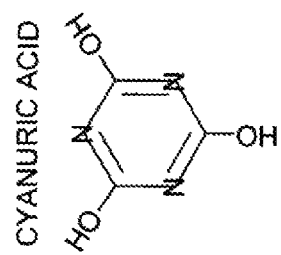
Figure 7:
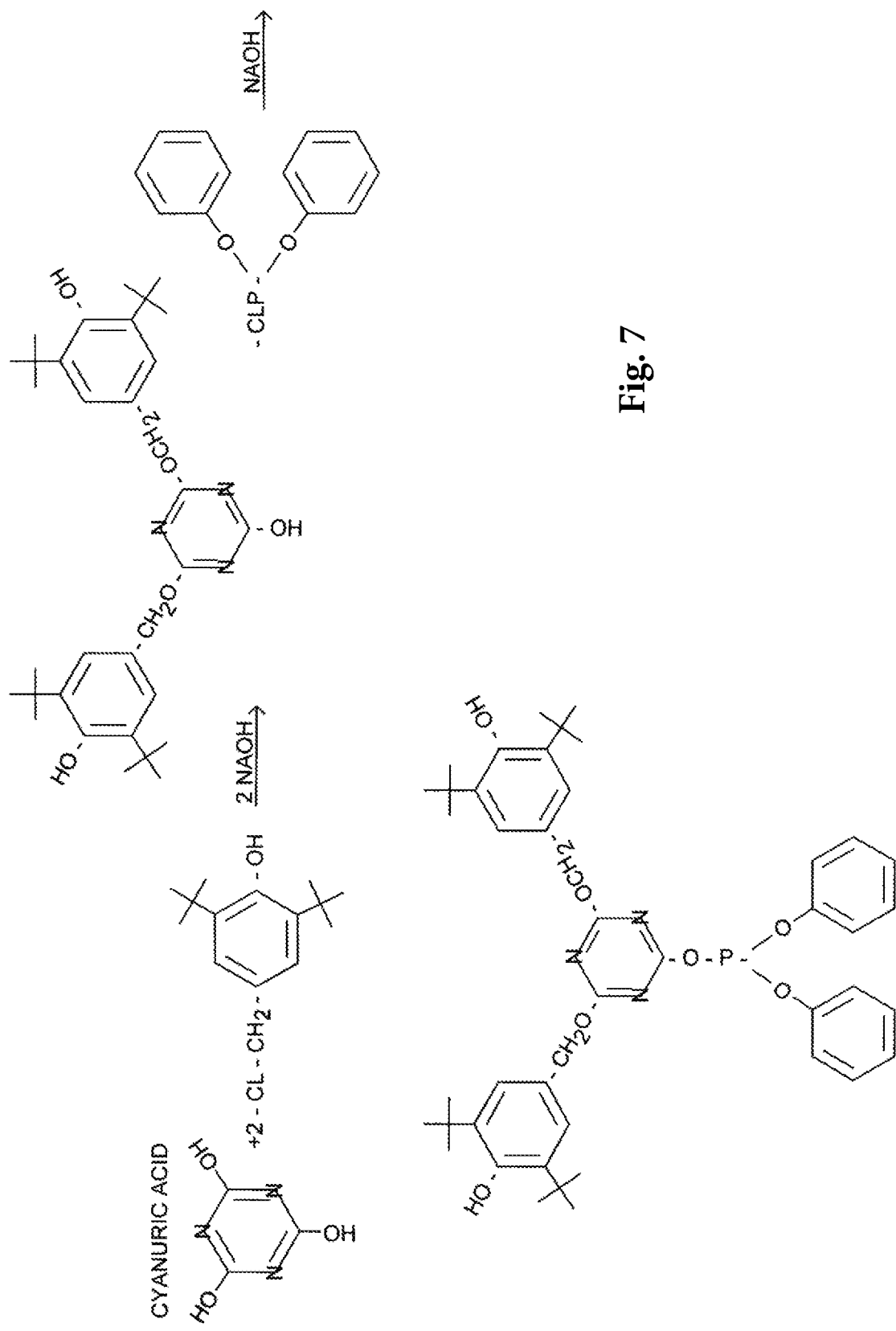
Figure 8:
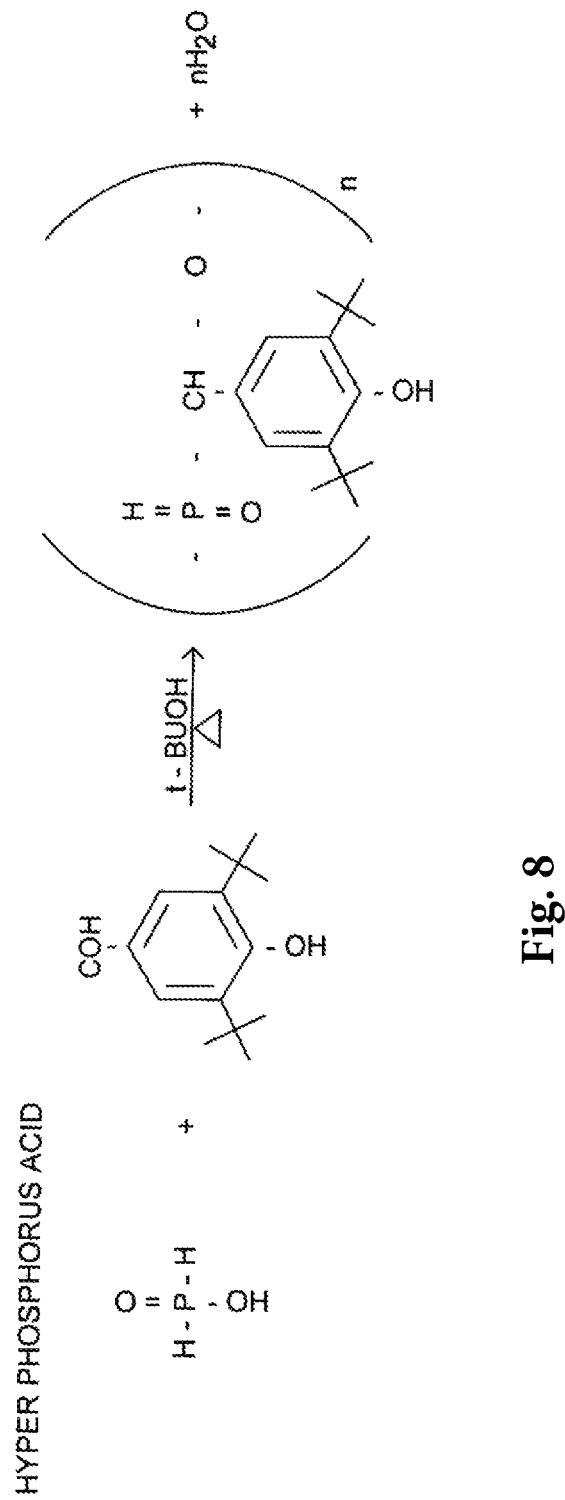
Figure 9:
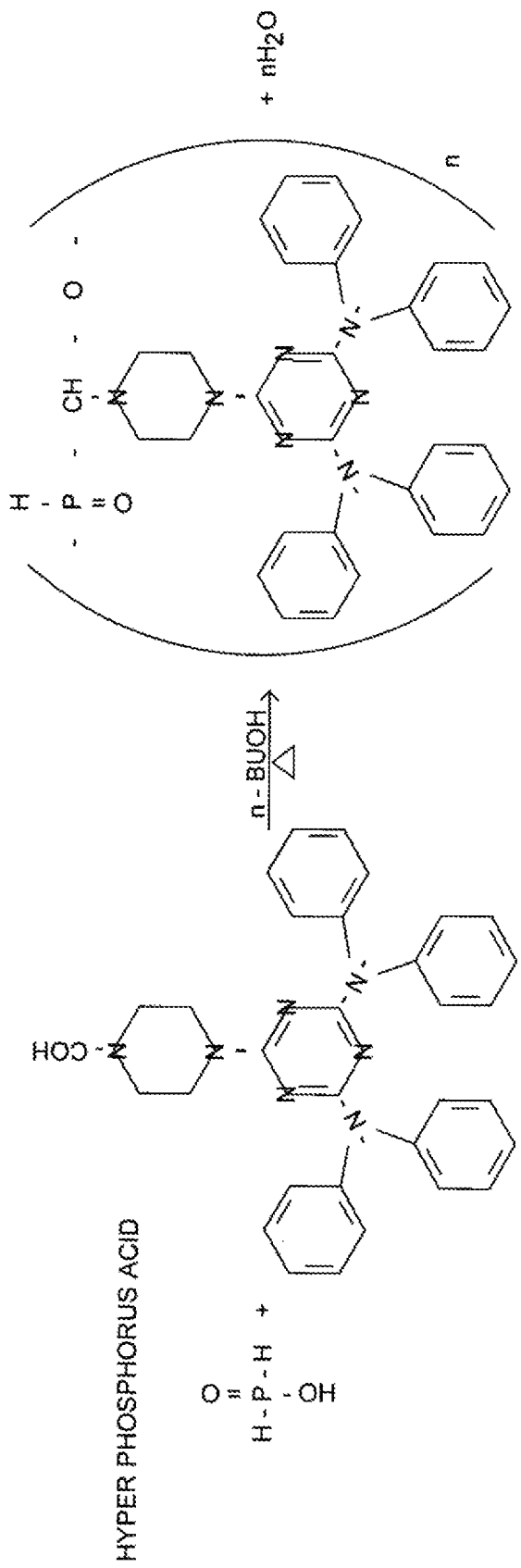
Figure 10:
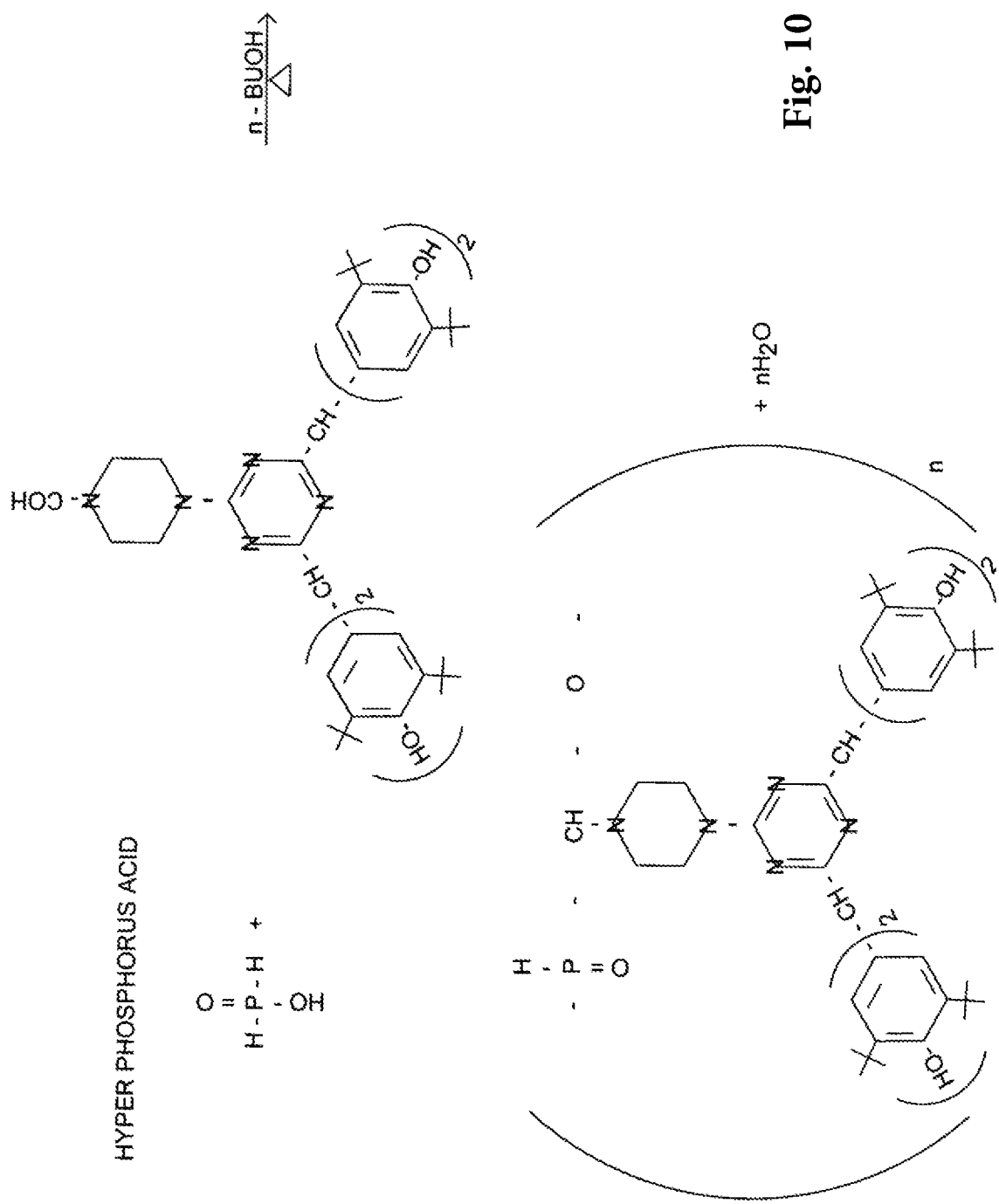
Figure 11:
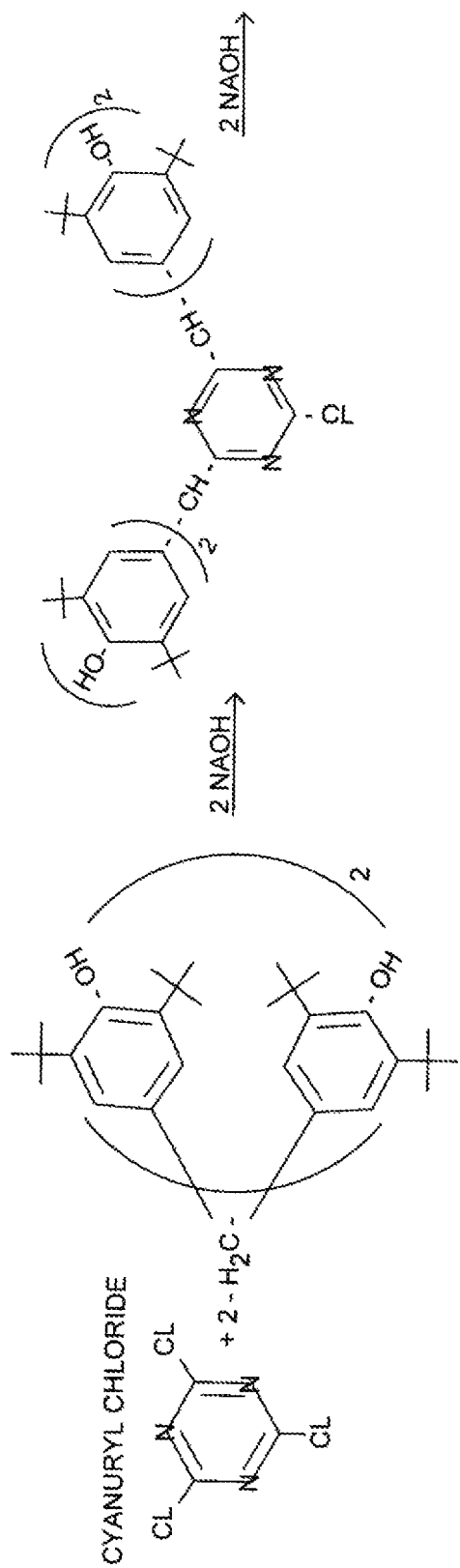
Figure 11:
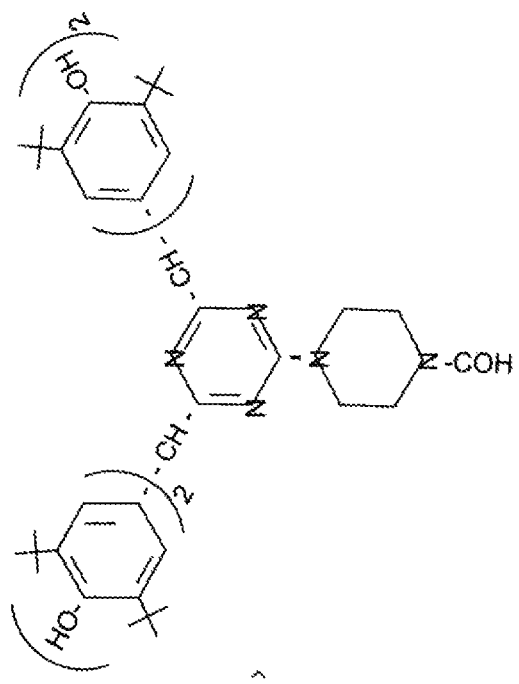
Figure 12:
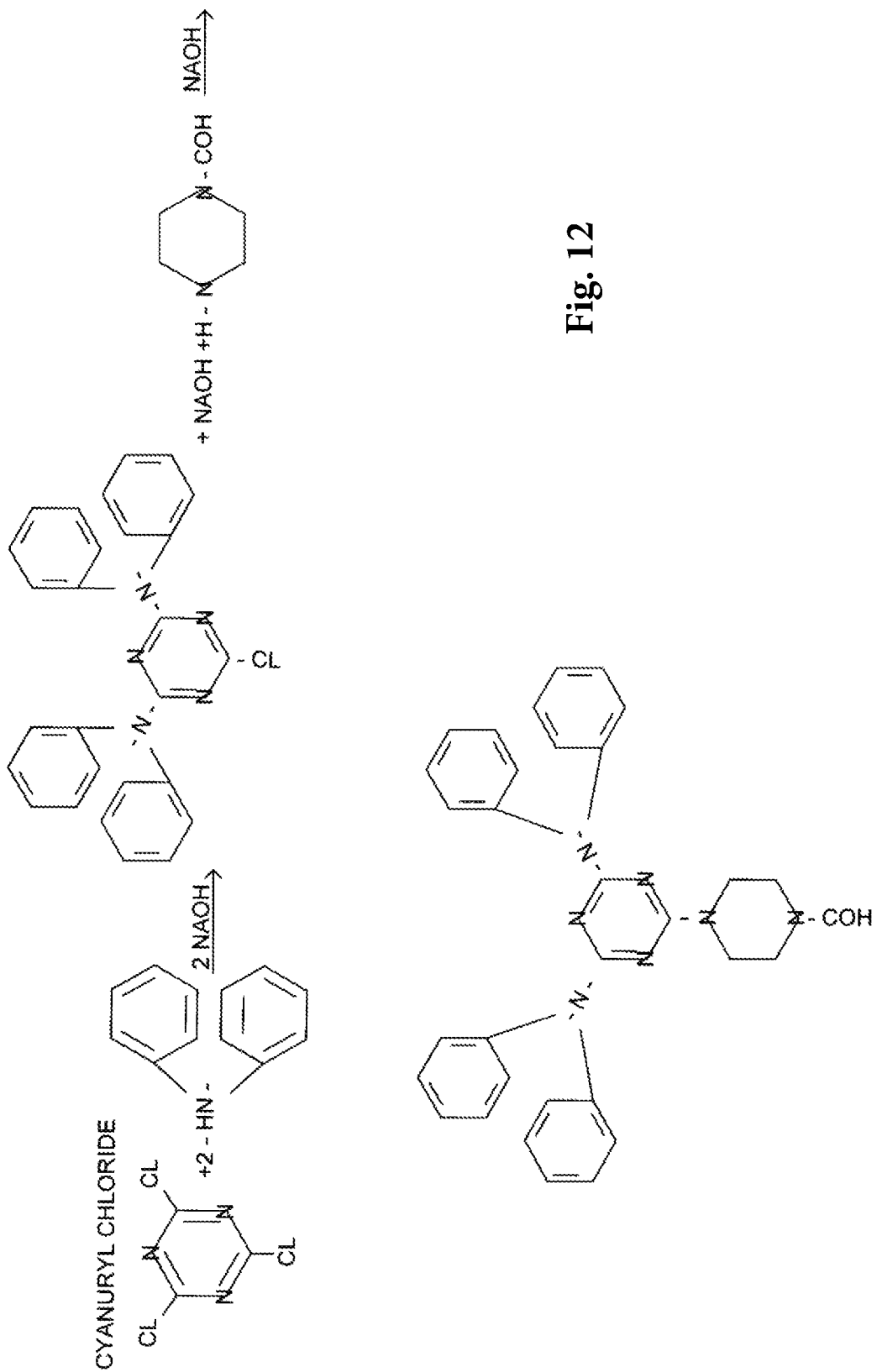
Figure 13:
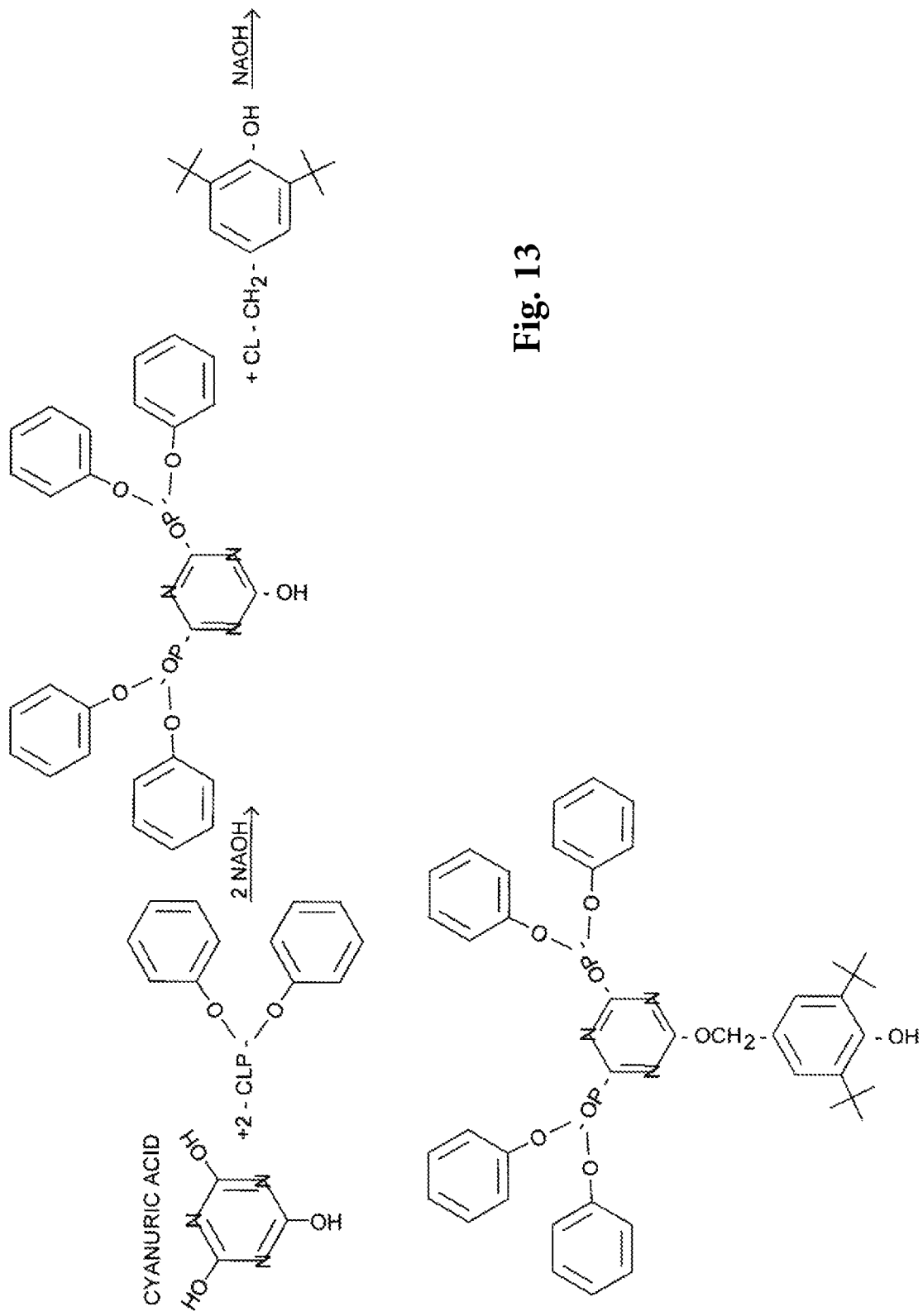

The present invention is predicated on the unexpected discovery that certain novel substituted triazines function as anti-oxidants for a variety of materials, particularly lubricating oils, and, most particularly, motor oils.

Exemplary substituted triazine compounds of the invention are:

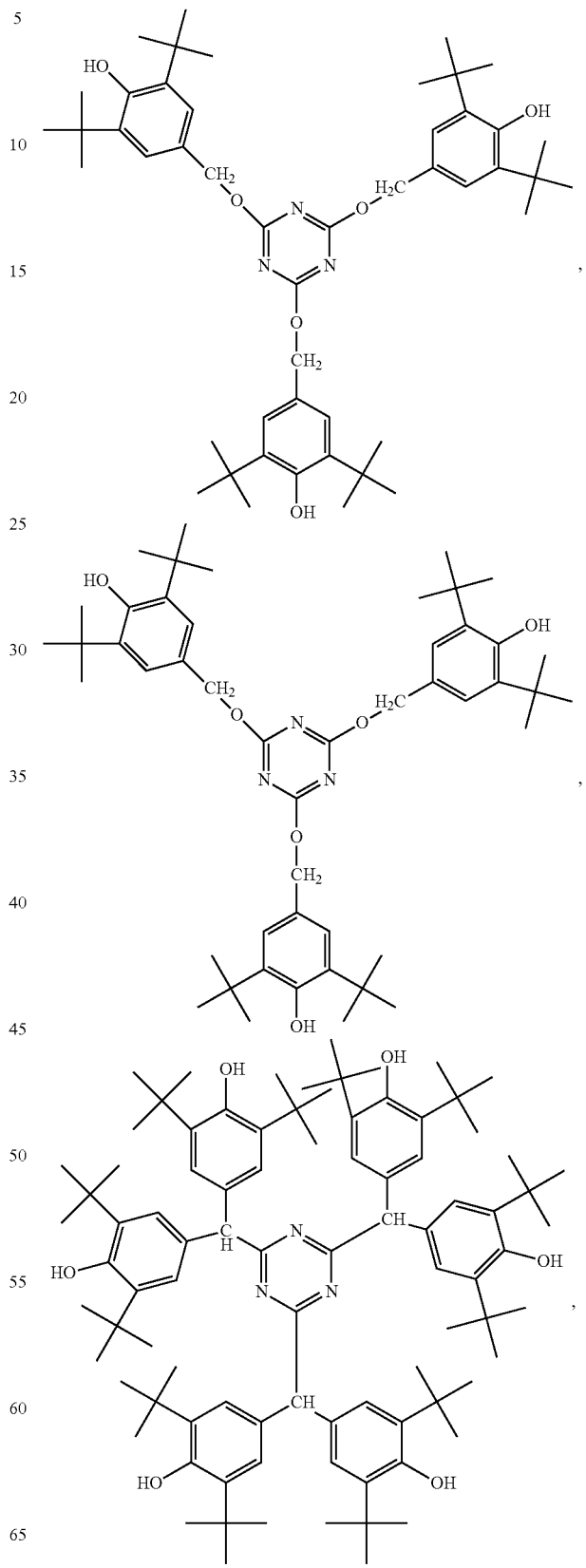

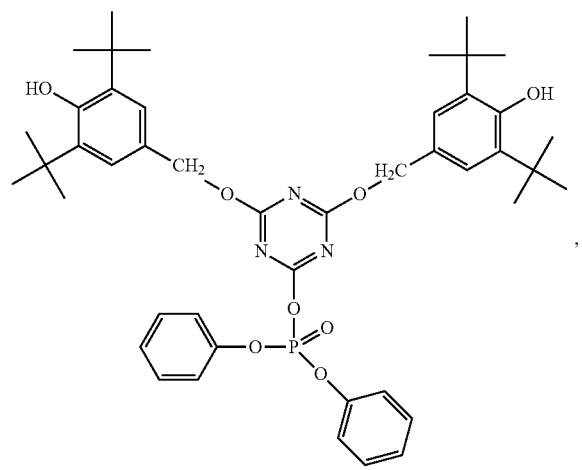

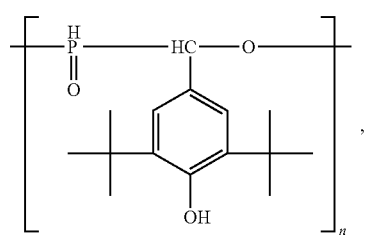

wherein n=1-10,

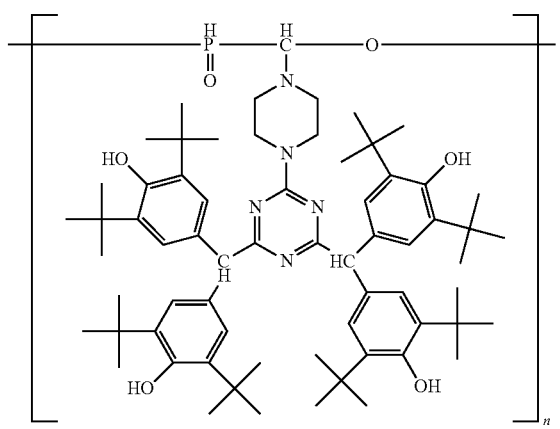

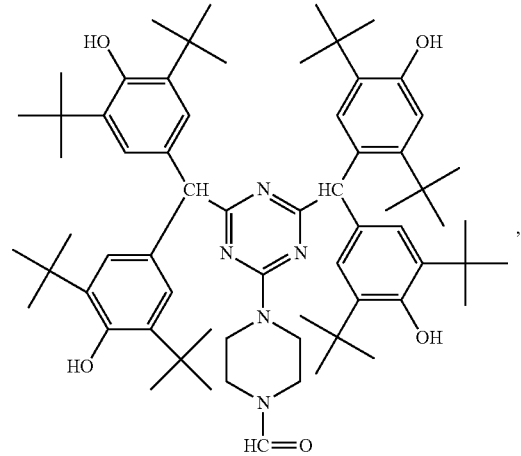

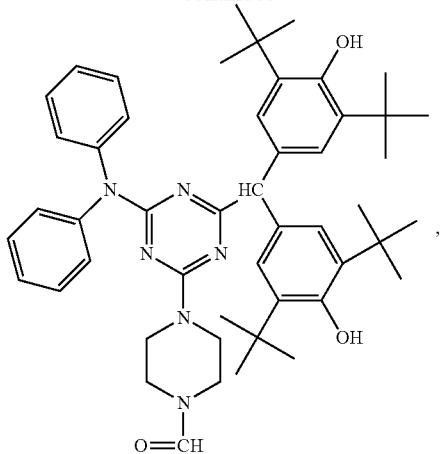

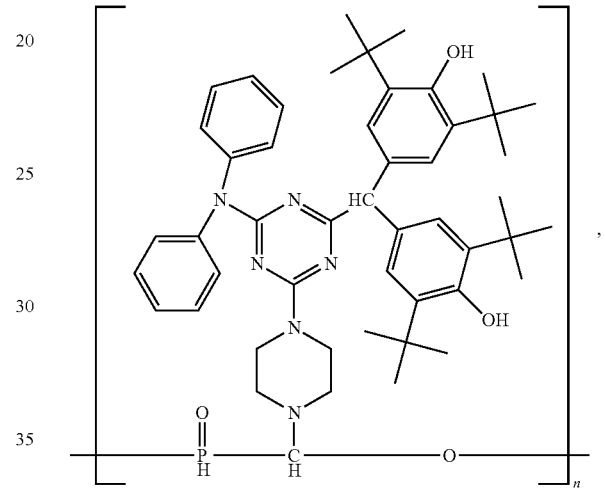

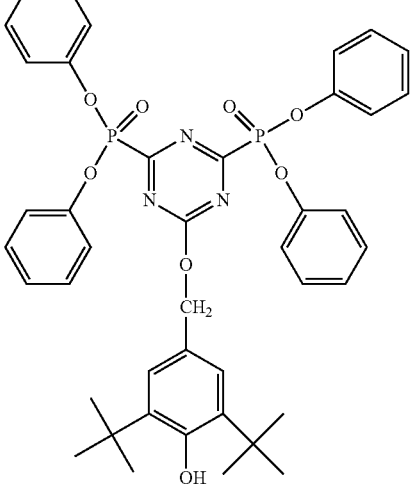

The above compounds are useful as anti-oxidants for any material with which they are physically and chemically compatible, including, but not limited to lubricant oils, paints and textiles.

Preferably, the compounds of the invention are useful as anti-oxidants for lubricating oils, and most preferably, motor oils, most particularly, internal combustion engine oils.

Any suitable lubricating oil viscosity may be stabilized with the antioxidants of the present invention, including, but not limited to those oils defined as American Petroleum Institute Groups I, II, and III, and can be of any suitable lubricating viscosity range, for example, having a kinematic viscosity range at 100° C. of about 1.5 centistokes (cSt) to about 1,000 cSt, and preferably about 2 cSt to about 100 cSt. Suitable oils include engine oils, transmission fluids, hydraulic fluids, gear oils, marine cylinder oils, compressor oils, refrigeration lubricants and mixtures thereof.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes; tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof.

Other useful synthetic lubricating oils include liquid polymers of alpha olefins having the proper viscosity. Especially useful synthetic ydrocarbon oils are the hydrogenated liquid oligomers of $C_6$ to $C_{18}$ alpha olefins such as, for example, 1-decene trimer.

Another class of useful synthetic lubricating oils include alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylenepolymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed C3-Ca fatty acid esters, or the C13 oxo acid diester of tetraethylene glycol.

Yet another class of useful synthetic lubricating oils include the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate di-n-hexyl fumarate, dioctyl sebacate, diisooctyl azelate, diisodecyl azelate, dioctyl phthalate, didecyl phthalate dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythrito, I and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicat, ehexyl-(4-methyl-2-pentoxy)disiloxane, poly(methyl)siloxanes, poly(methylphenyl)siloxane, sand the like. Still yet other useful synthetic lubricating oils include, but are not limited to, liquid esters of phosphorous containing esters, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties.

These purification techniques are known to those of skill in the art and include, for example, solvent extractions, secondary distillation, acid or base extraction, filtration, percolation, hydrotreating dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

If desired, the antioxidants described herein can be used in combination with other additives typically found in lubricating oils and such combinations may, in fact, provide synergistic effects toward improving desired properties, such as improved deposit control, anti-wear, frictional, antioxidant, low temperature, and like properties, to the lubricating oil. Examples of additives found in lubricating oils include, but are not limited to, antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, dispersants, dyes, extreme pressure agents and mixtures thereof. See, e.g., U.S. Pat. No. 5,498,809 for a description of useful lubricating oil composition additives. When employed with another additive in an additive package for a lubricating oil, the antioxidant described herein is typically present in an amount from 1 to about 75 weight percent of the additive package.

Useful dispersants include, but are not limited to, polyisobutylene succinimides, polyisobutylene succinate esters, Mannich Base ashless dispersants, and the like. Useful detergents include, but are not limited to, metallic alkyl phenates, sulfurized metallic alkyl phenates, metallic alkyl sulfonates, metallic alkyl salicylates, and the like. Useful antioxidant additives for use in combination with the additives of the present invention include, but are not limited to, alkylated diphenylamines, alkylated hindered phenolics, alkylated substituted or unsubstituted phenylenediamines, arylated substituted or unsubstituted phenylenediamines, alkylated oil soluble copper compounds, alkylated sulfur containing compounds known to impart oxidation stability and mixtures thereof. Suitable alkylated sulfur containing compounds known to impart oxidation stability include phenothiazine, sulfurized olefins, thiocarbamates, sulfur bearing hindered phenolics, zinc dialkyldithiophosphates and mixtures thereof.

Useful anti-wear additives for use in combination with the additives of the present invention include, but are not limited to, organo borates, organo phosphites, organic sulfur-containing compounds, zinc dialkyl dithiophosphates, zinc diaryl dithiophosphates, phosphosulfurized hydrocarbons, dialkyldithiophosphate ester, diaryl dithiophosphate ester and mixtures thereof. Useful friction modifiers for use in combination with the additives of the present invention include, but are not limited to, fatty acid esters and amides, organo molybdenum compounds, molybdenum dialkylthiocarbamates, molybdenum dialkyl dithiophosphates, molybdenum disulfide, tri-molybdenum cluster dialkyldithiocarbamate, non-sulfur molybdenum compound and mixtures thereof. Useful antifoaming agents include, but are not limited to, polysiloxane, and the like. An example of a rust inhibitor is polyoxyalkylene polyols, and the like.

Useful VI improvers include, but are not limited to, olefin copolymers and dispersant olefin copolymers, and the like. An example of a pour point depressant is polymethacrylate.

The compounds of the invention may be admixed directly with the material to be stabilized against oxidation, or they may first be combined with a compatible carrier, including, but not limited to, for example, dimethyl acetamide, benzotrichloride, and 2-methoxy-tetrahydropyran.

Typically, the antioxidants, whether or not first admixed with a carrier, are admixed with the material to be stabilize against oxidation in an amount, by weight of 0.005%-10%, preferably 0.2% to 0.5%.

The foregoing description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The invention claimed is:

1. An antioxidant compound having a formula selected from the group consisting of

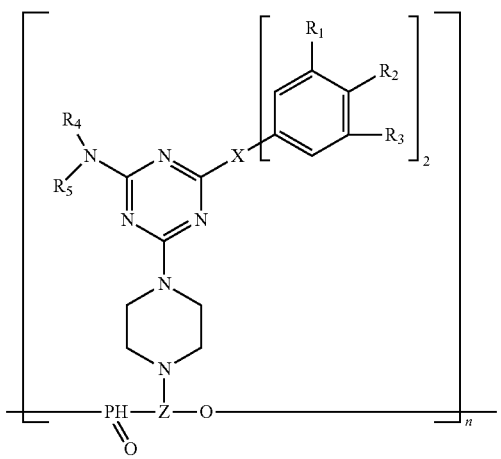

wherein

X and Z are each CH, $R_4$ and $R_5$ are the same or equal and are aryl groups, $R_1$ and $R_3$ are sterically hindering alkyl groups, $R_2$ is OH, and n=1-10,

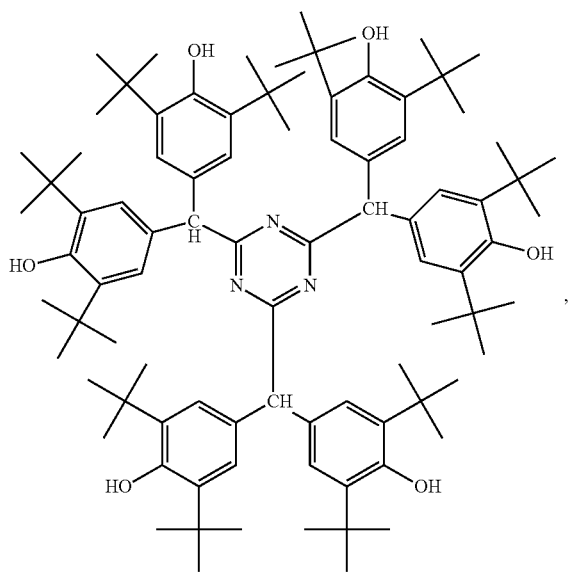

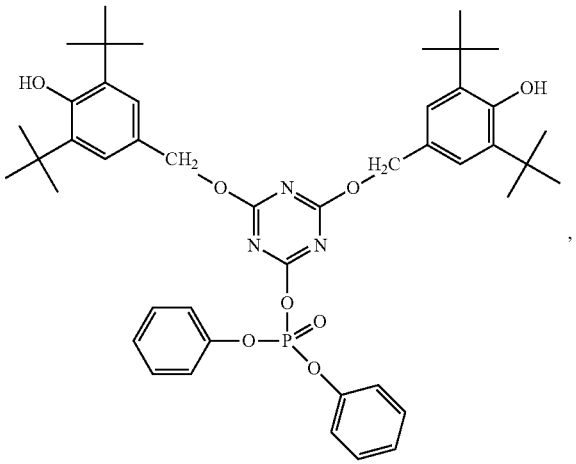

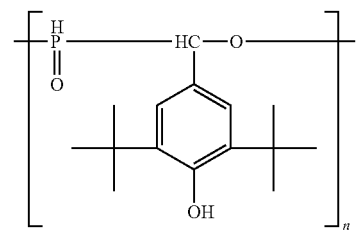

wherein n=1-10,

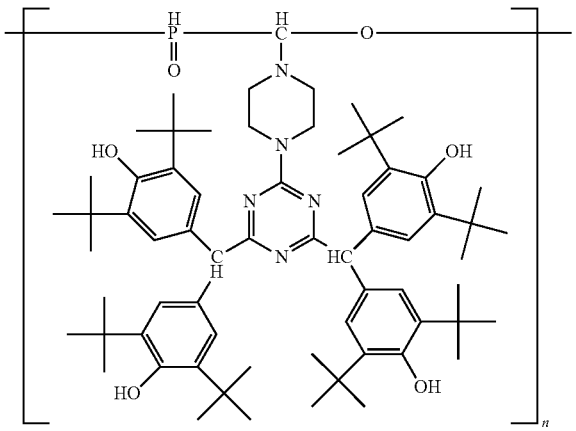

wherein n=-10,

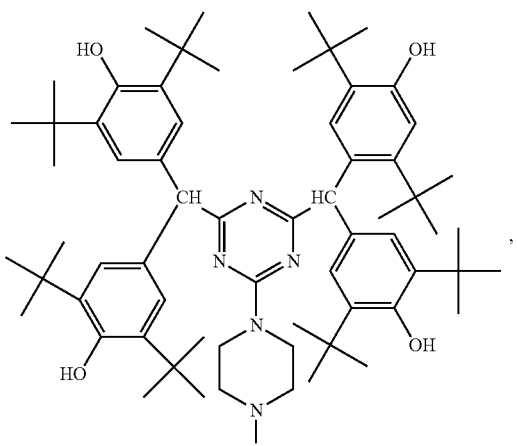

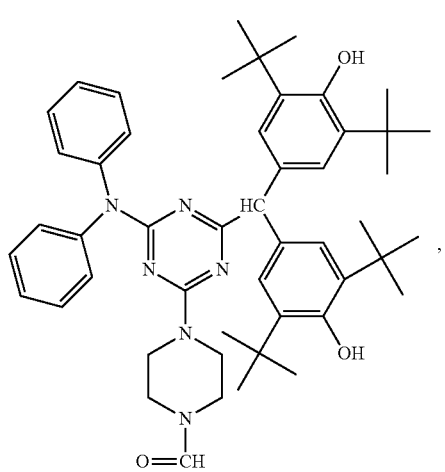

-continued

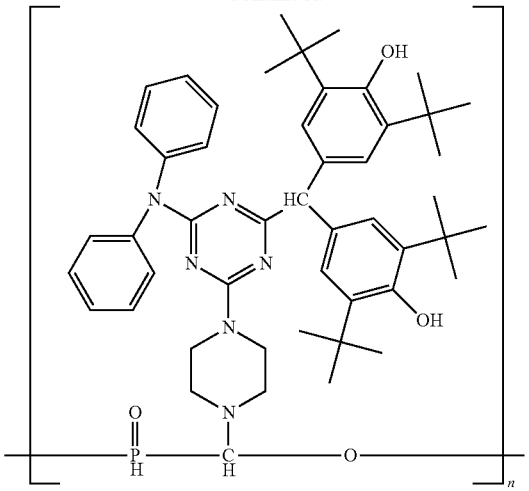

wherein n=1-10, and

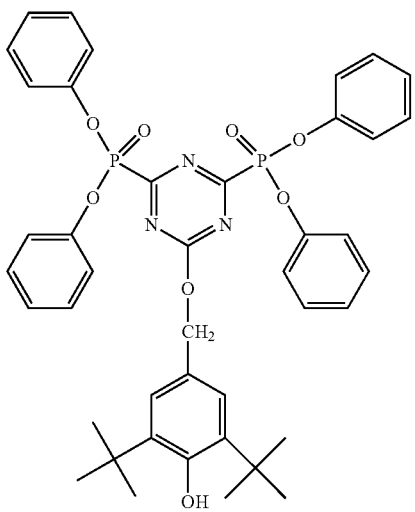

2. A composition of matter adapted for admixture with a material subject to deterioration by oxidation comprising a compound selected from the group consisting of a compound of claim 1 compatible with said material and a compatible carrier therefore.

3. A composition of matter comprising a material subject to oxidation and an antioxidant amount of a composition of claim 2.

4. A composition of matter comprising a material subject to oxidation and an anti-oxidant amount of a compound selected from the group consisting of a compound of claim 1.

5. A method of ameliorating the oxidation of a material comprising admixing therewith an antioxidant amount of a composition of claim 2, wherein said antioxidant compound is compatible with said material.

6. A method of ameliorating the oxidation of a material comprising admixing therewith an antioxidant amount of a compound of claim 1 compatible with said material and a carrier therefore.

7. An article of manufacture comprising packaging material containing the composition of claim 2, said packaging material containing instructions for the use thereof.

\* \* \* \* \*